(12) United States Patent
O'Rear et al.

(10) Patent No.: US 8,658,847 B2
(45) Date of Patent: Feb. 25, 2014

(54) PROCESSES AND COMPOSITIONS FOR THE INCORPORATION OF BIOLOGICALLY-DERIVED ETHANOL INTO GASOLINE

(75) Inventors: Dennis J. O'Rear, Sonoma, CA (US); Sven I. Hommeltoft, Pleasant Hill, CA (US); Hye-Kung Timken, Albany, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 368 days.

(21) Appl. No.: 12/817,341

(22) Filed: Jun. 17, 2010

(65) Prior Publication Data
US 2011/0308146 A1    Dec. 22, 2011

(51) Int. Cl.
*C07C 13/10* (2006.01)
*C07C 9/18* (2006.01)
*C07C 1/24* (2006.01)

(52) U.S. Cl.
USPC ............... 585/331; 585/240; 585/20; 585/16; 585/709; 44/451

(58) Field of Classification Search
USPC ............ 585/331, 240, 20, 16; 208/95; 44/451
See application file for complete search history.

(56) References Cited

U.S. PATENT DOCUMENTS

| | | | |
|---|---|---|---|
| 6,773,578 B1 | 8/2004 | O'Rear et al. | |
| 6,933,323 B2 | 8/2005 | O'Rear et al. | |
| 7,374,657 B2 | 5/2008 | Miller et al. | |
| 2003/0158456 A1* | 8/2003 | O'Rear et al. | 585/331 |
| 2010/0025292 A1* | 2/2010 | Hommeltoft et al. | 208/95 |

\* cited by examiner

*Primary Examiner* — Walter D Griffin
*Assistant Examiner* — Chantel Graham
(74) *Attorney, Agent, or Firm* — Tiffany E. Weksberg

(57) ABSTRACT

In the present invention, a biofuel composition and processes for the incorporation of biologically-derived ethanol into gasoline are disclosed. The present invention discloses ways to use biologically-derived ethanol in gasoline while simultaneously enabling the blending of products from saturation of benzene. In addition, the present invention also discloses ways to use this ethanol with other volatile compounds from petroleum such as isopentane.

9 Claims, 1 Drawing Sheet

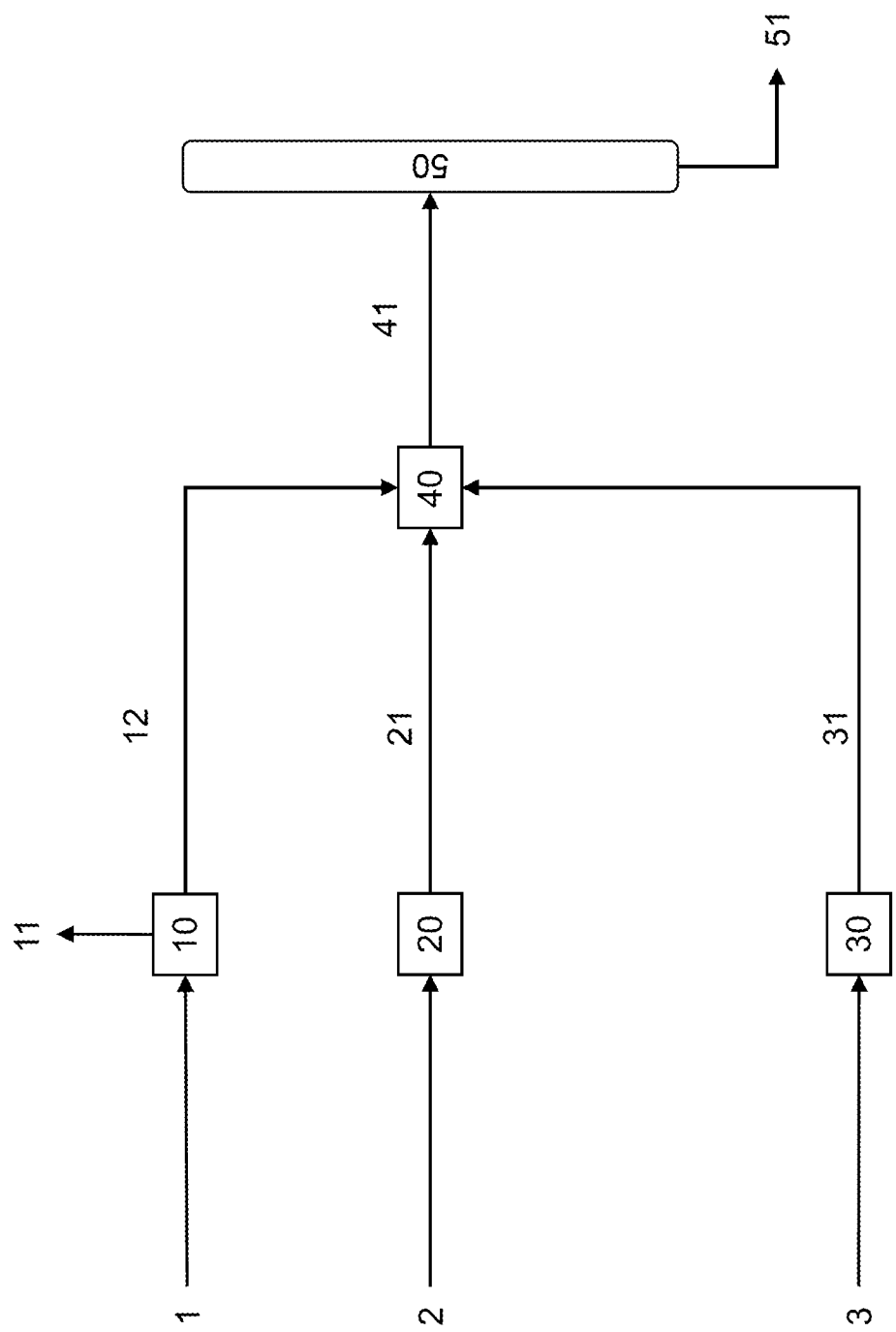

PROCESSES AND COMPOSITIONS FOR THE INCORPORATION OF BIOLOGICALLY-DERIVED ETHANOL INTO GASOLINE

FIELD OF THE INVENTION

The present invention relates generally to a biofuel composition and a process for making the same and specifically to processes for the incorporation of biologically-derived ethanol into gasoline.

BACKGROUND OF THE INVENTION

Gasoline and distillate fuels are regulated for a variety of reasons including, but not limited to, environmental concerns. For example, the U.S. Environmental Protection Agency (EPA) regulates hazardous air pollutants such as benzene from mobile sources. Specifically, the U.S. EPA has regulated the amount of benzene that gasoline may contain. Environmental concerns related to gasoline and distillate fuels are also addressed by the requirements to use renewable resources in the production of gasoline and distillate fuels.

Benzene occurs naturally in petroleum and is formed when petroleum naphtha is reformed to make high octane gasoline blending components. To reduce the benzene content, refiners have tried reducing the benzene-precursors in the feed to the naphtha reformers. However, when using this approach, benzene is still present in the gasoline blending components at levels that make it difficult to achieve regulated limits.

To reduce the benzene content, refiners have also taken two main approaches to meet the benzene limits by removing benzene in the gasoline blending components. They have (1) extracted the benzene and sold it as a petrochemical, and (2) hydrogenated the benzene in hydrocrackers and/or naphtha hydroisomerization units to form methylcyclopentane, cyclohexane, and mixtures thereof (cycloparaffins). The option to sell benzene is limited to locations where there is a market for this petrochemical. In addition, the price of benzene has decreased as many refiners have tried this solution. Given the limited market and low prices, many refiners have chosen instead to hydrogenate the benzene. However, one problem with hydrogenating the benzene is that the products from hydrogenating benzene are methylcyclopentane and cyclohexane. Both products are fairly volatile compounds and as a result can make meeting vapor pressure limits in gasoline difficult.

Unlike the requirements surrounding benzene, the requirements to incorporate renewable resources into the production of gasoline and distillate fuels are driven not just by environmental concerns but by supply concerns as well. For example, renewable resources can be used to produce ethanol which can then be added to gasoline. However, with the incorporation of ethanol in gasoline, gasoline still needs to comply with other specifications. Specifically, the Reid Vapor Pressure becomes a concern when volatile ethanol is blended into gasoline. As shown in Table 1 below, ASTM D4814 defines six Vapor Pressure/Distillation Classes for gasoline and the choice of the class depends on the location within the United States and the season. Colder climates (E) need more volatile gasoline for smooth starts while warmer climates (AA) need low volatile gasoline to avoid excessive evaporative losses and resulting air pollution.

TABLE 1

Vapor Pressure Specifications from ASTM D4814

| Class | Maximum Vapor Pressure (psia) |
|---|---|
| AA | 7.8 |
| A | 9.0 |
| B | 10.0 |
| C | 11.5 |
| D | 13.5 |
| E | 15.0 |

Adding small amounts of ethanol (less than 1%) into gasoline results in an additional 1 psi vapor pressure increase. The response is highly non-linear. The vapor pressure from 10% ethanol will approximately equal the vapor pressure maximum for warm climates. In this case, the vapor pressure of the other 90% must be very low.

As shown in Table 2 below, the products from the hydrogenation of benzene (cyclohexane and methylcyclopentane) have significant vapor pressures that can make blending with ethanol to make a specification fuel difficult, especially in warm climates. In addition to the products from hydrogenation of benzene, isopentane is a typical abundant component of petroleum. It too has a high vapor pressure and blending it with ethanol in gasoline is difficult. If pentanes cannot be blended into gasoline, alternative uses must be found, and those uses are typically low-value uses such as a feedstock for petrochemical production, for hydrogen production, or as a refinery fuel. Since refinery fuel is used as the feedstock for hydrogen production, both of the latter two options are low value options. In many locations, the option of selling pentanes into petrochemical use is not possible because of the distance from the market. In these cases, pentanes will be used as low-value refinery fuel.

TABLE 2

Properties of Relevant Gasoline Hydrocarbons

|  | RON | MON | RVP |
|---|---|---|---|
| Benzene | 98.0 | 90.0 | 3.224 |
| Cyclohexane | 83 | 77.1 | 3.263 |
| Methylcyclopentane | 91.3 | 80.0 | 4.503 |
| Methylcyclohexane | 74.8 | 71.1 | 1.608 |
| 1,1-Dimethylcyclopentane | 92.3 | 89.3 | 2.56 |
| 1,1-Dimethylcyclohexane | 87.3 | 85.8 | 0.82 |
| 1-Methyl, 1-ethylcyclopentane | 100.0 | 90.0 | 0.72 |
| 1-Methyl, 1-ethylcyclohexane | 76.7 | 68.7 | ~0.5 |
| Isopentane | 92.0 | 90.3 | 20.44 |
| 3,3-Dimethylpentane | 86.6 | 80.8 | ~2 |
| 2,3-Dimethylpentane | 91.1 | 88.5 | 2.35 |
| Ethanol | 112-120* | 95-106* | 50-100* |

(Above blending values in Table 2 are from the following: http://www.ec.gc.ca/cleanair-airpur/CAOL/transport/publications/ethgas/ethgas4.htm.)

Due to the need to lower the content of benzene in gasoline and distillate fuels and due to the need to incorporate renewable resources into the production of gasoline and distillate fuels, a way to incorporate both objectives would be useful. What is needed is a way to use biologically-derived ethanol in gasoline while simultaneously enabling the blending of products from the saturation of benzene. What is also needed is a way to use this ethanol with other volatile compounds from petroleum such as isopentane.

SUMMARY OF THE INVENTION

In the present invention, biofuel compositions and processes for the manufacture of partially biologically-derived alkylate for use as a gasoline or distillate fuel blending component are disclosed. The processes of the present invention comprise obtaining ethanol from a biological source such as grain and non-food agricultural products. Examples of non-food agricultural products include, but are not limited to, corn stover, switch grass, Miscanthus, Salix, Populus, rice hulls and stalks, forest waster, or other cellulosic material. The ethanol is then dehydrated to form ethylene and by-product water. In addition, as a part of the processes of the present invention, a benzene-containing naphtha is saturated in a naphtha isomerization unit to form a saturated naphtha that contains methylcyclopentane, cyclohexane and mixtures thereof (cycloparaffins). Next, the ethylene is alkyated with an isoparaffin, such as the cycloparaffins from the saturated naphtha, and an ionic liquid catalyst to form a partially biologically-derived alkylate.

BRIEF DESCRIPTION OF THE FIGURE

The description is presented with reference to the accompanying FIGURE in which:

FIG. 1 depicts a process flow diagram of one embodiment of the process of the present invention for the manufacture of partially biologically-derived alkylate for use as a gasoline or a distillate fuel blending component.

While the invention is susceptible to various modifications and alternative forms, specific embodiments thereof have been shown by way of example in the FIGURE and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

In the present invention, biofuel compositions and processes for the incorporation of biologically-derived ethanol into gasoline are disclosed. The present invention discloses ways to use biologically-derived ethanol in gasoline, or as a distillate fuel blending component, while also enabling the blending of products from saturation of benzene. In addition, the present invention also discloses ways to use this ethanol with other volatile compounds from petroleum such as isopentane.

1. Definitions

Certain terms are defined throughout this description as they are first used, while certain other terms used in this description are defined below:

"A Process to Saturate Benzene and Other Light Aromatics," as defined herein, is a process that uses hydrogen at super-atmospheric pressures in the presence of a catalyst to saturate at least a portion of the benzene in the feedstock to form cyclohexane, methylcyclohexane and mixtures thereof (cycloparaffins). Examples of this process are naphtha isomerization, hydrocracking, and hydrodewaxing.

"Alcohol Dehydration Process," as defined herein, may be accomplished by processing the feedstock over a catalyst, such as gamma alumina. During dehydration the alcohols are converted into olefins such as ethylene. U.S. Pat. No. 6,933,323 includes an example of this process. In this example, metal oxides are used at elevated temperatures.

"Blending Component," as defined herein, is a hydrocarbonaceous liquid used with other blending components to make a specification transportation fuel, such as motor gasoline, aviation gasoline, jet fuel, and diesel fuel. The blending component by itself does not need to meet all the specified properties of the specification transportation fuel, but should be of use in forming the specified fuel when blended with other components. As the percentage of the blending component increases, its properties must approach those of the specification transportation fuel. Blending components can be at or between 0.1 and 99.9 wt % of the specification transportation fuel. For example, the blending component can be at or between 1 and 99%, at or between 5 and 95%, at or between 10 and 90%, at or between 20 and 80%, at or between 30 and 70%, et cetera.

"C5+, C6+, C8+," et cetera, as used herein, means that a certain stream contains hydrocarbons predominantly of this carbon number and/or greater. However, due to the imprecision of refinery operations, the stream can also contain small amounts of lower carbon number hydrocarbons. In this context, predominantly means that the content of lower carbon number hydrocarbons is less than 10 wt %, for example, less than 5 wt %, less than 2 wt %, or less than 1 wt %.

"Conventional Hydrodewaxing," as defined herein, is a Catalytic Dewaxing process that uses a Conventional Hydrodewaxing Catalyst. In Conventional Hydrodewaxing, the pour point is lowered by selectively cracking the wax molecules, mostly to smaller paraffins boiling between propane and about octane. Since this technique converts the wax to less valuable by-products, it is useful primarily for dewaxing oils that do not contain a large amount of wax. Waxy oils of this type are frequently found in petroleum distillate from moderately waxy crudes. Catalysts that are useful for Conventional Hydrodewaxing are typically 12-ring zeolites and 10-ring zeolites. Zeolites of this class include ZSM-5, ZSM-11, ZSM-22, ZSM-23, ZSM-35, and Mordenite. Conventional Hydrodewaxing catalysts favor cracking in comparison to other method of conversion of paraffins. In addition to the zeolites, metals may be added to the catalyst, primarily to reduce fouling. U.S. Pat. No. 6,773,578 includes an example of this process.

"Hydrocracking," as defined herein, is a process for breaking longer carbon chain molecules into smaller ones. Hydrocracking may be conducted according to conventional methods known to those of skill in the art, but with control over the conditions for hydrocracking such that a distillate fuel product comprising a moderate amount of aromatics and the above-described properties is provided. The hydrocracking process is effected by contacting the particular fraction or combination of fractions, with hydrogen in the presence of a suitable hydrocracking catalyst at a suitable temperature. The hydrocracking process according to the present invention is conducted at temperatures in the range of from about 600 to 900° F. (316 to 482° C.), preferably at a temperature of greater than 650° F. (343 to 454° C.), more preferably at a temperature of greater than 700° F., even more preferably at a temperature of greater than 725° F. Still more preferably, the hydrocracking process according to the present invention is conducted at a temperature of about 725 to 800° F. The hydrocracking process according to the present invention is conducted at a pressure of less than or equal to 3,000 psia, preferably less than or equal to 2,500 psia, even more preferably less than or equal to 1,500 psia, and even more preferably less than or equal to 1,000 psia. The hydrocracking process according to the present invention is conducted using space velocities based on the hydrocarbon feedstock of about 0.1 to 2.0 $hr^{-1}$, preferably 0.2 to 1.0 $hr^{-1}$, more preferably 0.5 to 0.75 $hr^{-1}$. The hydrocracking process according to the present invention is conducted with hydrogen being added at a rate of 1 to 20 MSCF/B (thousand standard cubic feet per barrel), preferably 2 to 10 MSCF/B, and more preferably 5 to 7.5 MSCF/B. U.S. Pat. No. 7,374,657 includes an example of this process.

"Hydroisomerization," as defined herein involves contacting a waxy hydrocarbon stream with a catalyst, which contains an acidic component, to convert the normal and slightly branched iso-paraffins in the waxy stream to other non-waxy species and thereby generate a lube base stock product with an acceptable pour point. The contacting of the waxy stream and catalyst may be carried out in the presence of hydrogen. Typical conditions under which the hydroisomerization process may be carried out include temperatures from about 200 to 400° C. and pressures from about 15 to 3000 psig. The liquid hourly space velocity during contacting is generally from about 0.1 to 20. The hydrogen to hydrocarbon ratio falls within a range from about 1.0 to about 50 moles $H_2$ per mole hydrocarbon. Hydroisomerization converts at least a portion of the waxy feed to non-waxy iso-paraffins by isomerization, while at the same time minimizing conversion by cracking. The degree of cracking is limited so that the yield of less valuable by-products boiling below the lubricant base oil range is reduced and the yield of lubricant base oil is increased. Hydroisomerization generates a lubricant base oil with higher VI and greater oxidation and thermal stability. In the hydroisomerization process, the waxy feed is contacted under isomerization conditions.

"Hydroprocessing," as defined herein, generally refers to reactions in the presence of a catalyst and hydrogen at high temperature and pressure for modification of hydrocarbonaceous material by saturation, isomerization, heteroatom removal, cracking, and the like. Hydrocracking and hydrotreating are examples of hydroprocessing reactions.

"Hydrotreating," as defined herein, is a process for removing impurities, such as elemental sulfur, nitrogen, or oxygen or compounds containing, sulfur, nitrogen, or oxygen, from a hydrocarbonaceous product mixture. Hydrotreating also saturates olefins and aromatics that can be present in Fischer-Tropsch products to form hydrotreated distillate blending components. Typical hydrotreating conditions vary over a wide range. In general, the overall LHSV (liquid hourly space velocity) is about 0.25 to 6.0, preferably about 0.5 to 3.0. The hydrogen partial pressure is greater than 200 psia, preferably ranging from about 500 psia to about 2000 psia. Hydrogen recirculation rates are typically greater than 50 SCF/Bbl, and are preferably between 1000 and 5000 SCF/Bbl. Temperatures range from about 300° F. to about 900° F., preferably ranging from 450° F. to 800° F.

"Ionic Liquids," as defined herein, are liquids that are composed entirely of ions as a combination of cations and anions. Ionic liquids may be suitable for use as a catalyst and as a solvent in alkylation and polymerization reactions as well as in dimerization, oligomerization, acetylation, metatheses, and copolymerization reactions. All components do not necessarily need to be reacted in one system. For example, separate reactors can be used to react low molecular weight olefins with high molecular weight iso- and cyclo-paraffins.

"Ionic Liquid Catalysts," as defined herein, are a class of ionic liquids. Ionic Liquid Catalyst are fused salt compositions which are molten at low temperature and are useful as catalysts, solvents and electrolytes. Such compositions are mixtures of components which are liquid at temperatures below the individual melting points of the components. The so-called "low temperature" ionic liquids are generally organic salts with melting points under 100° C. and often even lower than room temperature. Examples of such low temperature ionic liquids or molten fused salts are the chloroaluminate salts. Alkyl imidazolium or pyridinium salts, for example, can be mixed with aluminum trichloride ($AlCl_3$) to form the fused chloroaluminate salts.

"Naphtha," as defined herein, is a light hydrocarbon fraction used in the production of gasoline, solvents, and as a feedstock for ethylene production which contains material boiling above pentane, and typically has an end point below about 500° F.

"Naphtha Isomerization," as defined herein, can use either an amorphous catalyst support such as a silica-alumina or $AlCl_3$ or it can use a molecular size such as a zeolite. In naphtha hydroisomerization normal paraffins are converted primarily into tertiary isoparaffins and the quantity of quaternary isoparaffins (neopentane, 2,2-dimethylbutane, etc) is 25 wt % or less, for example 10% or less; or 5% or less.

"Specification Transportation Fuel," as defined herein, is a transportation fuel including, but not limited to, motor gasoline, aviation gasoline, jet fuel, and diesel fuel that conforms to at least one of the following standards:

a. Diesel Fuel: A material suitable for use in diesel engines and conforming to the current version of at least one of the following specifications: ASTM D-975, "Standard Specification for Diesel Fuel Oils" European Grade CEN 90 Japanese Fuel Standards JIS K 2204 The United States National Conference on Weights and Measures (NCWM) 1997 guidelines for premium diesel fuel The United States Engine Manufacturers Association recommended guideline for premium diesel fuel (FQP-1A).
  b. Distillate Fuel: A material containing hydrocarbons with boiling points between about 60 and 1100° F. The term "distillate" means that typical fuels of this type can be generated from vapor overhead streams of petroleum crude distillation. In contrast, residual fuels cannot be generated from vapor overhead streams of petroleum crude distillation, and are a non-vaporizable remaining portion. Within the broad category of distillate fuels are specific fuels that include: naphtha, jet fuel, diesel fuel, kerosene, aviation gasoline, fuel oil, and blends thereof.
  c. Gasoline: A material suitable for use in spark-ignition internal-combustion engines for automobiles and light trucks (motor gasoline) and piston engine aircrafts (aviation gasoline) meeting the current version of at least one of the following specifications: ASTM D-4814 for motor gasoline European Standard EN 228 for motor gasoline Japanese Standard JIS K2202 for motor gasoline ASTM D-910 for aviation gasoline ASTM D-6227, "Standard Specification for Grade 82 Unleaded Aviation Gasoline" UK Ministry of Defence Standard 91-90/Issue 1 (DERD 2485), GASOLINE, AVIATION: GRADES 80/87, 100/130 and 100/130 LOW LEAD.
  d. Jet Fuel: A material suitable for use in turbine engines for aircrafts or other uses meeting the current version of at least one of the following specifications: ASTM D-1655 DEF STAN 91-91/3 (DERD 2494), TURBINE FUEL, AVIATION, KEROSINE TYPE, JET A-1, NATO CODE: F-35 International Air Transportation Association (IATA) "Guidance Material for Aviation Turbine Fuels Specifications," 4th edition, March 2000 United States Military Jet fuel specifications MIL-DTL-5624 (for JP-4 and JP-5) and MIL DTL-83133 (for JP-8).

2. Biofuel Compositions And Processes For Manufacture

In the present invention, biofuel compositions and processes for the manufacture of partially biologically-derived ethanol for use as a gasoline or distillate fuel blending component are disclosed.

In order to incorporate renewable resources into gasoline, biologically-derived ethanol may be blended into gasoline or may be used as a distillate fuel blending component. The present invention discloses processes for the incorporation of biologically-derived ethanol into gasoline. Ethanol may be obtained from a biological source such as grain and/or non-food agricultural products. Examples of non-food agricultural products include, but are not limited to, corn stover, switch grass, Miscanthus, Salix, Populus, rice hulls and stalks, forest waster, or other cellulosic material. However, ethanol is volatile and therefore, impacts the vapor pressure limits of gasoline. As part of the processes of the present invention, the ethanol is dehydrated to form ethylene and by-product water.

The processes of the present invention also enable the blending of volatile products from the saturation of benzene into gasoline. Benzene occurs naturally in petroleum and is formed when petroleum naphtha are reformed to make high octane gasoline blending components. The benzene-containing naphtha can be obtained from a number of petrochemical manufacture sources including, but not limited to, an FCC unit, a reforming unit, a coking unit, toluene dealkylation, toluene disproportionation, ethylbenzene dealkylation as occurs in xylene isomerication, and combinations thereof. In order to reduce the amount of benzene in gasoline, benzene is often hydrogenated to form a saturated naphtha that contains methylcyclopentane, cyclohexane, and mixtures thereof (cycloparaffins). These hydrogenation products are volatile compounds which impact the vapor pressure limits of gasoline.

In addition, the processes of the present invention also enable the incorporation of other volatile compounds from petroleum such as isopentane into the biofuel composition of the present invention.

The processes of the present invention utilize ionic liquid catalysts. Unlike conventional alkylation catalysts, ionic liquid catalysts can alkylate ethylene with isoparaffins and cycloparaffins, such as the cycloparaffins from the saturated naphtha, to form less volatile hydrocarbons. The alkylation of these hydrocarbons permits these hydrocarbons to be converted into less volatile hydrocarbons and thus the ethylene can be incorporated into the gasoline in a less volatile form. Unlike conventional sulfuric acid ($H_2SO_4$) and hydrofluoric acid (HF), ionic liquids can alkylate ethylene. Unlike these conventional acids, ionic liquid catalysts can also alkylate cycloparaffins and isopentane with little cracking to form light products such as butanes. By utilizing these processes, a partially biologically-derived alkylate will be formed.

One embodiment of the present invention is depicted in FIG. 1. In FIG. 1, biologically-derived ethanol 1 is dehydrated over an alumina catalyst at elevated temperatures in a dehydrogenation unit 10 to form water 11 and ethylene 12. A benzene-containing naphtha 2 is saturated in a naphtha isomerization unit 20 to form a saturated naphtha that contains methylcyclopentane 21. A vacuum gas oil 3 is hydrocracked in a hydrocracker 30 to form isopentane 31. The ethylene 12, methylcyclopentane 21, and isopentane 31 are alkylated in an alkylation reactor 40 that contains a chloroaluminate ionic liquid catalyst to form an effluent 41. The effluent is distilled in a distillation column 50 to recover the partially biologically-derived alkylate 51.

Optionally, the partially biologically-derived alkylate 51 may be further blended with additional biologically-derived ethanol. This additional blending may be used in order to meet both the oxygenate requirements of fuels and the requirements for fuel carbon intensity.

In another embodiment (not shown), only one of the methylcyclopentane or isopentane streams is alkylated with the ethylene.

Some of the hydrocarbons produced from the processes of the present invention differ from the hydrocarbons typically present in petroleum naphtha. For example, the alkylate product from methylcyclopentane is 1-methyl, 1-ethylcyclopentane and isomers of this product. As shown in Table 1, this has a RON of 100 and MON of 90 with a RVP of less than 1 psia. Studies have reported the content of 1-methyl,1-ethylcyclopentane from <0.01% to 0.06 wt %. Chromatographic standards vary from 1.076 wt. % to 1.5 wt % of this component; however, a chromatographic standard is not used for a material intended for commercial use as a gasoline blending component.

The process of the present invention creates a partially biologically-derived alkylate. The biological origin of the alkylate can be determined using ASTM D6866-08 (Determining the Biobased Content of Natural Range Materials Using Radiocarbon and Isotope Ratio Based Mass Spectrometry Analysis) which will express the percent biological component as percent Modern Carbon (pMC). Modern carbon has a higher $^{14}C$ content than "fossil" carbon found in petroleum, shale oil, coal and other fossil fuel resources. ASTM D6866-08 has three methods (A, B and C). In one embodiment of the present invention, Method B of ASTM D6866-08 is used when there is a question about the validity of the other two methods.

The partially biologically-derived alkylate of the present invention is composed of two carbon atoms from the biologically-derived ethylene and from four to seven carbon atoms from the non-biological isoparaffin; as a result, the maximum pMC should be between 22 and 33. However, according to ASTM D6866-08, pure biological carbon materials can have pMC values greater than 100. Therefore, alkylates of this invention will have a maximum pMC of 40. Alkylates of the present invention may also contain unreacted isoparaffin. In conventional propylene-isobutane alkylation, isobutane is processed in excess and the unreacted portion is distilled and recycled. In the present invention it may be difficult to distill the unreacted isoparaffin from the partially-derived alkylate and it may not be necessary to do so. Thus the pMC of the alkylate of one embodiment of the present invention will be greater than or equal to 1 and less than or equal to 40. For example greater than or equal to 2 and less than or equal to 20; or greater than or equal to 5 and less than or equal to 10.

When the partially biologically-derived alkylate is blended with other components to form a fuel meeting California requirements for carbon intensity, the pMC will be equal to or greater than 1, for example, greater than 2, greater than 4, or greater than 6. In these instances, the pMC will still be less than 40.

When the partially biologically-derived alkylate is present in blends with other biologically-derived compounds, such as ethanol, the pMC of the alkylate component can be determined by use of gas chromatograph-mass spectrometric (GC-MS) techniques. These techniques measure the $^{14}C$ content of individual compounds and thus the pMC of the alkylate can be determined. In mixtures such as this, alkylate is defined as all isoparaffins having between six and nine carbon atoms.

In addition, in another embodiment of the present invention, other biologically derived alcohols (C2+) could be used in lieu of biologically-derived ethanol. For example, biologically-derived butanol can be hydrogenated to butane and can be alkylated.

Illustrative embodiments of the invention are described above. In the interest of clarity, not all features of an actual embodiment are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover it will be appreciated that such a development effort might be complex and time-consuming, but would nevertheless be a routine undertaking for those of ordinary skill in the art having the benefit of this disclosure.

What is claimed is:

1. A method to manufacture a partially biologically-derived alkylate comprising:
   obtaining ethanol from a biological source;
   converting said ethanol into ethylene by an alcohol dehydration process;
   obtaining petroleum-derived hydrocarbons selected from the group consisting of cycloparaffins, isoparaffins, and combinations thereof;
   alkylating said ethylene with said petroleum-derived hydrocarbons to form an effluent; and
   recovering a partially biologically-derived alkylate from said effluent.

2. The method of claim 1 wherein said cycloparaffins comprise hydrocarbons selected from the group consisting of cyclohexane, methylcyclopentane, methylcyclohexane, and combinations thereof.

3. The method of claim 2 wherein said cycloparaffins are formed by hydrogenation of benzene by processes selected from the group consisting of hydrocracking, naphtha hydroisomerization, and combinations thereof.

4. The method of claim 1 wherein said isoparaffins comprise hydrocarbons selected from the group consisting of isobutane, isopentane, isohexane, isoheptanes, isooctanes, and combinations thereof.

5. The method of claim 1 wherein pMC of said partially biologically-derived alkylate is greater than or equal to 1 and less than or equal to 40.

6. The method of claim 1 wherein said alkylating step further comprises use of an ionic liquid catalyst.

7. The method of claim 6 wherein said ionic liquid catalyst is a chloroaluminate.

8. The method of claim 1 wherein said recovery step comprises distillation.

9. The method of claim 1 further comprising a step of blending of said partially biologically-derived alkylate with said ethanol from a biological source.

\* \* \* \* \*